(12) United States Patent
Sano et al.

(10) Patent No.: US 11,337,641 B2
(45) Date of Patent: May 24, 2022

(54) HARDNESS METER AND METHOD HAVING HARDNESS ESTIMATION PORTION THAT ESTIMATES HARDNESS OF MEASUREMENT OBJECT BASED ON ALTERNATING CURRENT COMPONENT

(71) Applicant: Maxell, Ltd., Kyoto (JP)

(72) Inventors: Yuko Sano, Tokyo (JP); Akihiko Kandori, Tokyo (JP); Mitsuo Okimoto, Tokyo (JP); Shigemitsu Ando, Oyamazaki (JP); Mitsunobu Watanabe, Oyamazaki (JP)

(73) Assignee: MAXELL, LTD., Kyoto (JP)

( * ) Notice: Subject to any disclaimer, the term of this patent is extended or adjusted under 35 U.S.C. 154(b) by 345 days.

(21) Appl. No.: 16/470,964

(22) PCT Filed: Dec. 15, 2017

(86) PCT No.: PCT/JP2017/045045
§ 371 (c)(1),
(2) Date: Jun. 18, 2019

(87) PCT Pub. No.: WO2018/116968
PCT Pub. Date: Jun. 28, 2018

(65) Prior Publication Data
US 2019/0313962 A1    Oct. 17, 2019

(30) Foreign Application Priority Data
Dec. 19, 2016    (JP) .............................. JP2016-245528

(51) Int. Cl.
*G01N 3/40* (2006.01)
*A61B 5/00* (2006.01)

(52) U.S. Cl.
CPC .............. *A61B 5/442* (2013.01); *A61B 5/743* (2013.01); *G01N 3/40* (2013.01);
(Continued)

(58) Field of Classification Search
CPC ... G01N 2203/0019; G01N 2203/0032; G01N 2203/0083; G01N 2203/0218;
(Continued)

(56) References Cited

U.S. PATENT DOCUMENTS

| 5,911,694 A | 6/1999 | Ikeda et al. |
| 2013/0085417 A1* | 4/2013 | Kan ..................... A61B 5/0053 600/587 |

(Continued)

FOREIGN PATENT DOCUMENTS

| JP | H05-264427 A | 10/1993 |
| JP | H05-322731 A | 12/1993 |

(Continued)

OTHER PUBLICATIONS

Chinese Office Action dated Feb. 23, 2021 for Chinese Patent Application No. 201780067016.6.
International Search Report for PCT/JP2017/045045.

*Primary Examiner* — Brandi N Hopkins
(74) *Attorney, Agent, or Firm* — Volpe Koenig

(57) ABSTRACT

The objective of the present invention is to provide a hardness meter which estimates hardness in a stable manner regardless of a compression strength. Disclosed is a hardness meter characterized in being provided with: a movable portion which is continuously pressed against an object to be measured; a sensor which outputs an output signal reflecting a reaction force at a part of the object to be measured that is in contact with the movable portion; a motive force mechanism that causes the movable portion to perform a piston motion; and a hardness estimating portion which estimates the hardness of the object to be measured on the basis of an alternating current component of the output signal, generated by the piston motion of the movable portion.

10 Claims, 14 Drawing Sheets

(52) U.S. Cl.
CPC .............. *A61B 2562/0219* (2013.01); *A61B 2562/0223* (2013.01); *A61B 2562/0247* (2013.01); *G01N 2203/0005* (2013.01); *G01N 2203/0019* (2013.01); *G01N 2203/0032* (2013.01); *G01N 2203/0083* (2013.01); *G01N 2203/0218* (2013.01); *G01N 2203/0617* (2013.01)

(58) Field of Classification Search
CPC .... G01N 2203/0617; G01N 3/08; G01N 3/42; G01N 33/50; A61B 5/107
See application file for complete search history.

(56) References Cited

U.S. PATENT DOCUMENTS

| | | | | |
|---|---|---|---|---|
| 2014/0250989 | A1* | 9/2014 | Tsujii | G01N 3/42 73/81 |
| 2015/0285722 | A1* | 10/2015 | Wu | G01N 3/42 73/82 |
| 2018/0177448 | A1 | 6/2018 | Zhang et al. | |

FOREIGN PATENT DOCUMENTS

| | | |
|---|---|---|
| JP | H10-062328 A | 3/1998 |
| JP | 2001-212087 A | 8/2001 |
| JP | 2011-130805 A | 7/2011 |
| JP | 2013-076658 A | 4/2013 |
| JP | 2013-212177 A | 10/2013 |
| WO | 2016/194468 A1 | 12/2016 |

\* cited by examiner

F I G. 1 2

| EXAMINEE REGISTRATION SCREEN | |
|---|---|
| EXAMINEE ID | P0000001 (ALPHANUMERIC CHARACTER INPUT) |
| EXAMINEE NAME | HITACHI TARO (TEXT INPUT) |
| GENDER | MALE (SELECT MALE/FEMALE) |
| AGE | 71 (NUMBER INPUT) |
| DISEASE INFORMATION | BACKACHE (TEXT INPUT) |
| THERAPY INFORMATION | ACUPUNCTURE THERAPY, ELECTRIC THERAPY (TEXT INPUT) |
| OTHER INSPECTION RESULTS | ******* (TEXT INPUT) |

FIG. 13
(a)
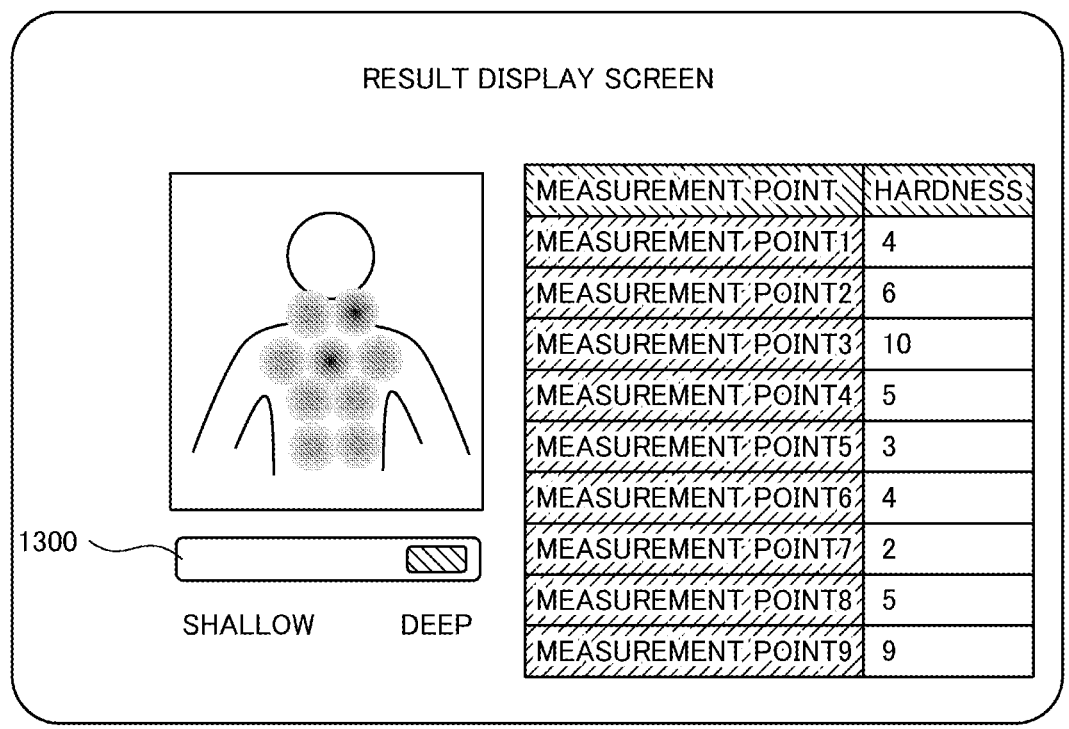
(b)
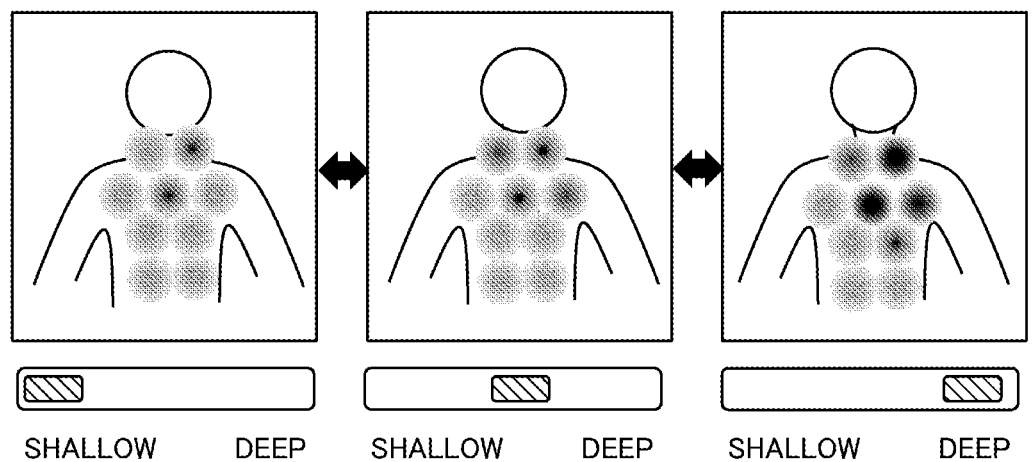

F I G. 1 4 A

| DIRECT CURRENT COMPONENT AMPLITUDE | DEPTH (mm) |
|---|---|
| 10 mV | 2 |
| 20 mV | 4 |
| 30 mV | 6 |
| ⋮ | ⋮ |

(a)

| ALTERNATING CURRENT COMPONENT AMPLITUDE | HARDNESS |
|---|---|
| 10 mV | 4 |
| 20 mV | 6 |
| 30 mV | 8 |
| ⋮ | ⋮ |

(b)

F I G. 1 4 B

SHALLOW PART: DIRECT CURRENT COMPONENT = 100 mV

| ALTERNATING CURRENT COMPONENT AMPLITUDE | DEPTH (mm) |
|---|---|
| 10 mV | 4 |
| 20 mV | 6 |
| 30 mV | 8 |
| ⋮ | ⋮ |

(a)

DEEP PART: DIRECT CURRENT COMPONENT = 200 mV

| ALTERNATING CURRENT COMPONENT AMPLITUDE | HARDNESS |
|---|---|
| 10 mV | 2 |
| 20 mV | 3 |
| 30 mV | 4 |
| ⋮ | ⋮ |

(b)

FIG. 16
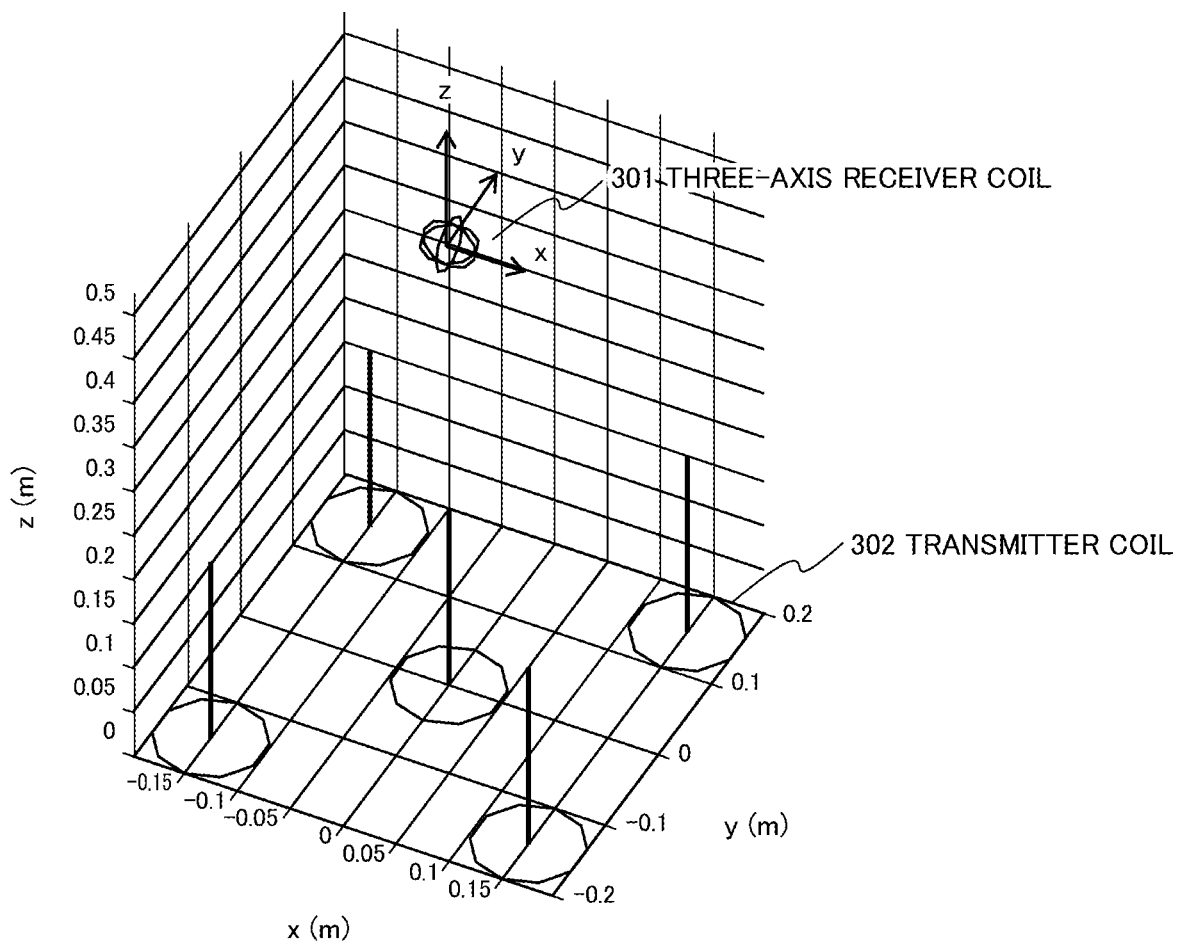
ATTITUDE OF THREE-AXIS RECEIVER COIL
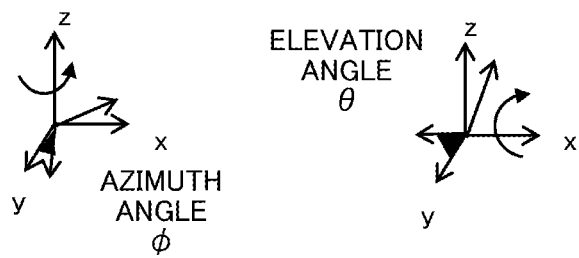

HARDNESS METER AND METHOD HAVING HARDNESS ESTIMATION PORTION THAT ESTIMATES HARDNESS OF MEASUREMENT OBJECT BASED ON ALTERNATING CURRENT COMPONENT

TECHNICAL FIELD

The present invention relates to a hardness meter that estimates hardness of an object.

BACKGROUND ART

Conventionally, there are many situations where measuring hardness of an object is beneficial. For example, it is desired to achieve measurement of the hardness of a human body in a field of medicine and a field of cosmetics. In the field of medicine, measuring the hardness of a predetermined position ensures determination of, for example, ulcer of skin on a support surface and edema or scleroderma of skin due to change in organ, which are caused by a longtime bedridden state in an identical posture. In an acupuncture and moxibustion clinic, an orthopedic clinic, and the like, it is possible to determine an effect that an acupuncture and moxibustion therapy and an osteopathy make a muscle flexible. In the field of cosmetics, measuring the hardness of a predetermined position ensures determination of, for example, an extent of illness and an effect when a medical therapy is performed.

For such use, conventionally, a measuring instrument referred to as a durometer that takes a degree of depression of the object when the object is compressed at a constant force as an indicator of the hardness has been used. Further, a tactile sensor that obtains change information of a resonant state when a mechanical vibrator contacts a substance to output the change information as hardness information of the substance has been developed (see PLT 1).

CITATION LIST

Patent Literature

PLT 1: Japanese Patent Application Laid-Open No. Hei 10-062328

SUMMARY OF INVENTION

Technical Problem

As a problem of the aforementioned durometer, there is a problem that a force with which a person compresses the object changes the degree of depression of the object as a measurement result. That is, even if it is the identical object, the estimated hardness differs between when the object is lightly compressed and when the object is strongly compressed. Therefore, the present invention solves this problem with a hardness meter including a mechanism that causes a pressure sensor to actively perform periodic motion, in addition to a mechanism of a durometer.

Solution to Problem

One aspect of the present invention is a hardness meter including a movable portion, a sensor, a motive force mechanism, and a hardness estimating portion. The movable portion is continuously pressed against an object to be measured. The sensor outputs an output signal reflecting a reaction force at a part of the object to be measured that is in contact with the movable portion. The motive force mechanism causes the movable portion to perform a piston motion. The hardness estimating portion estimates the hardness of the object to be measured on the basis of an alternating current component of the output signal, generated by the piston motion of the movable portion.

Another aspect of the present invention is a hardness measuring method including a first step of vibrating a movable portion, a second step of obtaining a sense signal on the basis of a reaction force from an object to be measured when the movable portion is caused to contact the object to be measured, a third step of obtaining an alternating current component of the sense signal, and a fourth step of estimating hardness of the object to be measured on the basis of an amplitude of the alternating current component.

Advantageous Effects of Invention

With the present invention, the hardness meter ensures estimation of the hardness from only an output value of the pressure sensor without depending on a strength of compression by an operator. Problems, configurations, and effects other than the above-described ones will be made apparent from the description of the following embodiment.

BRIEF DESCRIPTION OF DRAWINGS

FIG. 12 is a diagram of an examinee registration screen.

FIG. 13 includes diagrams illustrating the estimated hardness and a hardness map in a result display screen.

FIG. 14A includes tables illustrating exemplary correspondence tables in an embodiment.

FIG. 14B includes tables illustrating other exemplary correspondence tables in the embodiment.

FIG. 16 is a schematic diagram illustrating a measurement device for position estimation.

DESCRIPTION OF EMBODIMENTS

The following describes an embodiment of the present invention with reference to the attached drawings. The attached drawings illustrate a specific embodiment in line with the principle of the present invention. However, they are for understanding of the present invention and not necessarily used for interpreting the present invention in a limited way. In the respective drawings, identical reference numbers may be attached to the common configurations.

The following embodiment relates to a technique to calculate hardness of an object to be measured. The hardness is an indicator that represents hardness of the object to be measured and means elasticity. In the following, a description will be given by exemplifying a living body such as a human body as the object to be measured, but the object to be measured is not limited to it. For example, a hardness meter in the following embodiment may be applied to an object other than the living body.

Figure 1:
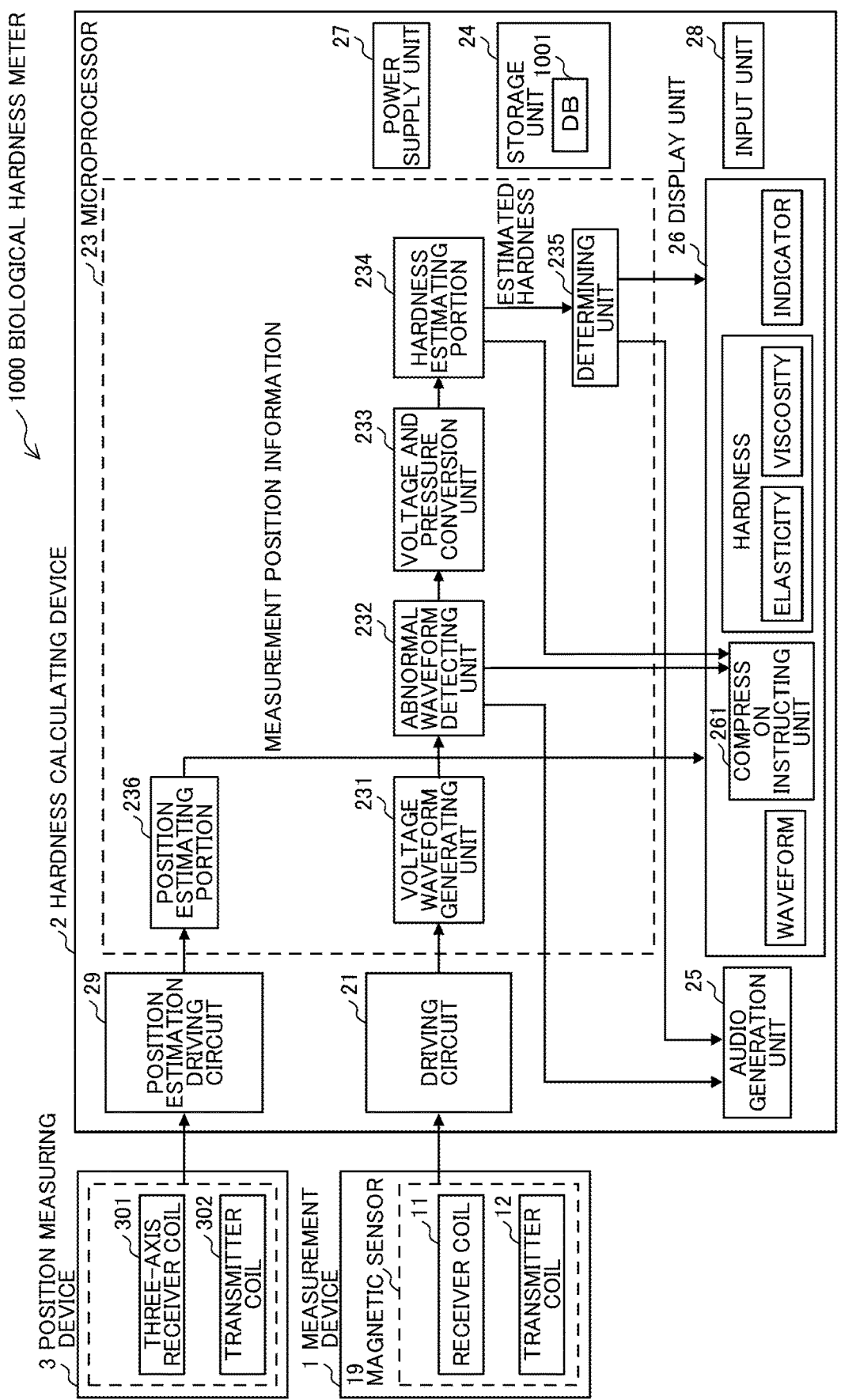
FIG. 1 is a block diagram of an overall configuration of a biological hardness meter.

FIG. 1 is an overall configuration drawing of a biological hardness meter. A biological hardness meter 1000 includes a measurement device 1 and a hardness calculating device 2. In the measurement device 1 in FIG. 1, compared with the measurement devices 1 in FIG. 2, FIG. 3, and FIG. 4, a part of the configuration is not illustrated. Here, by referring to FIG. 2, FIG. 3, and FIG. 4 together, a description will be given of a configuration and an operating principle of the measurement device 1.

Figure 2:
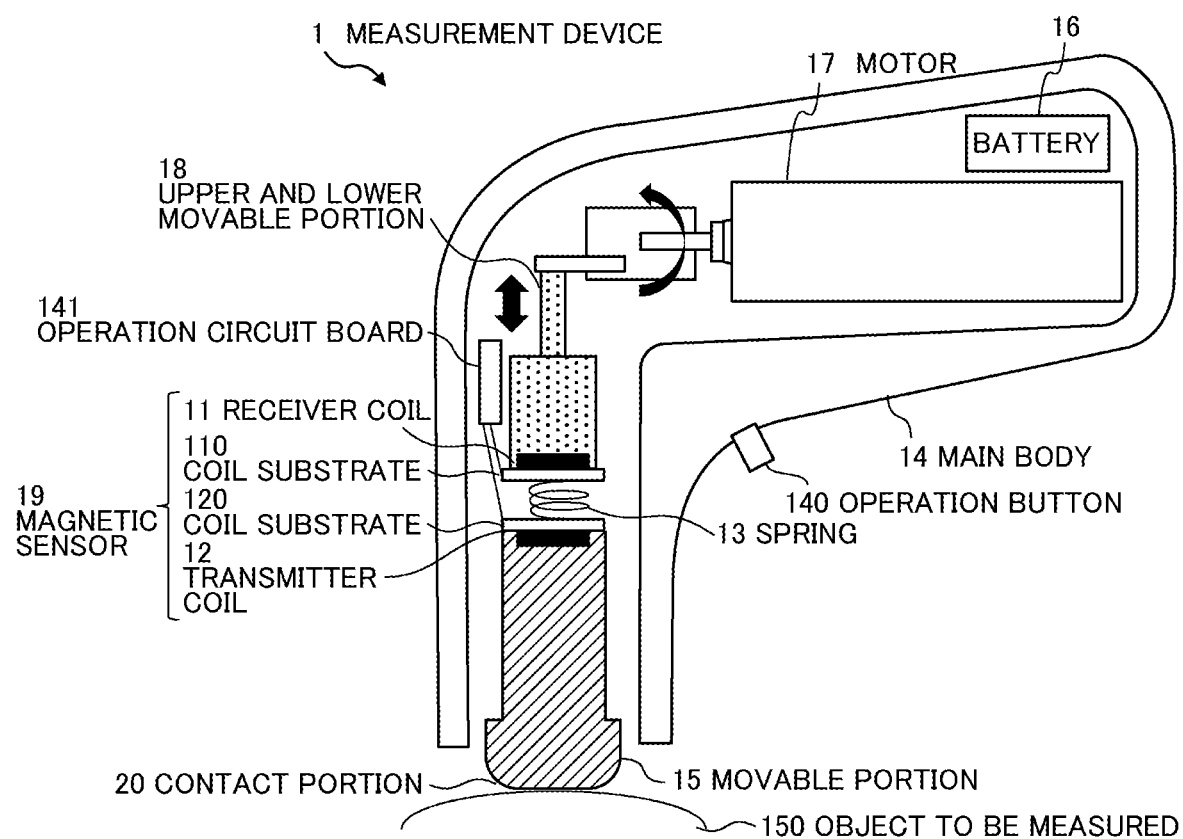
FIG. 2 is a description perspective view of an exemplary structure of a measurement device (gun type).

FIG. 2 illustrates an exemplary configuration of the measurement device 1. The measurement device 1 includes a main body 14 including a receiver coil 11 (magnetic field detecting means), a movable portion 15 including a transmitter coil 12 (magnetic field generating means), a spring 13 (elastic body), a battery 16, a motor 17, and an upper and lower movable portion 18. It is a configuration where the motor 17 driven by the battery 16 causes the upper and lower movable portion 18 to perform a piston motion with, for example, a crank structure. A combination of the motor 17 and the upper and lower movable portion 18 being a motive force mechanism. A combination of the receiver coil 11 and the transmitter coil 12 is referred to as a magnetic sensor 19. The magnetic sensor 19 outputs reaction force information corresponding to a reaction force at a part of an object 150 to be measured that is in contact with the movable portion 15.

The movable portion 15 has a contact portion 20 that is a part pressed against the object 150 to be measured so that the object 150 to be measured is depressed when the hardness is measured (calculated) and a contact surface of a movable portion and an object portion. The main body 14 and the movable portion 15 have stiffnesses. The object 150 to be measured is, for example, any object whose hardness is desired to be measured including a trunk of a person.

The magnetic sensor 19 outputs information on a voltage in proportion to a magnitude of the reaction force of the object 150 to be measured corresponding to a pressure applied to the object 150 to be measured by the measurement device 1. Therefore, the receiver coil 11 and the transmitter coil 12 are arranged opposed to one another. The spring 13 having a spring constant of K' (already-known) is arranged between the main body 14 and the movable portion 15 (see FIG. 2).

The spring 13 may be exchanged for a spring having a thick wire diameter in an identical shape. This ensures measurement of the hardness at a deep layer position of the object. Conventionally, only the measurement of the hardness on a skin surface has been performed, thus having a problem that the measurement of the hardness cannot respond to information on up to the deep layer of the skin. In contrast, the configuration has a possibility that the measurement of the hardness can be performed on not only the skin surface but also a subcutaneous tissue, a muscle, and the like up to the deep layer of the skin.

Figure 3:
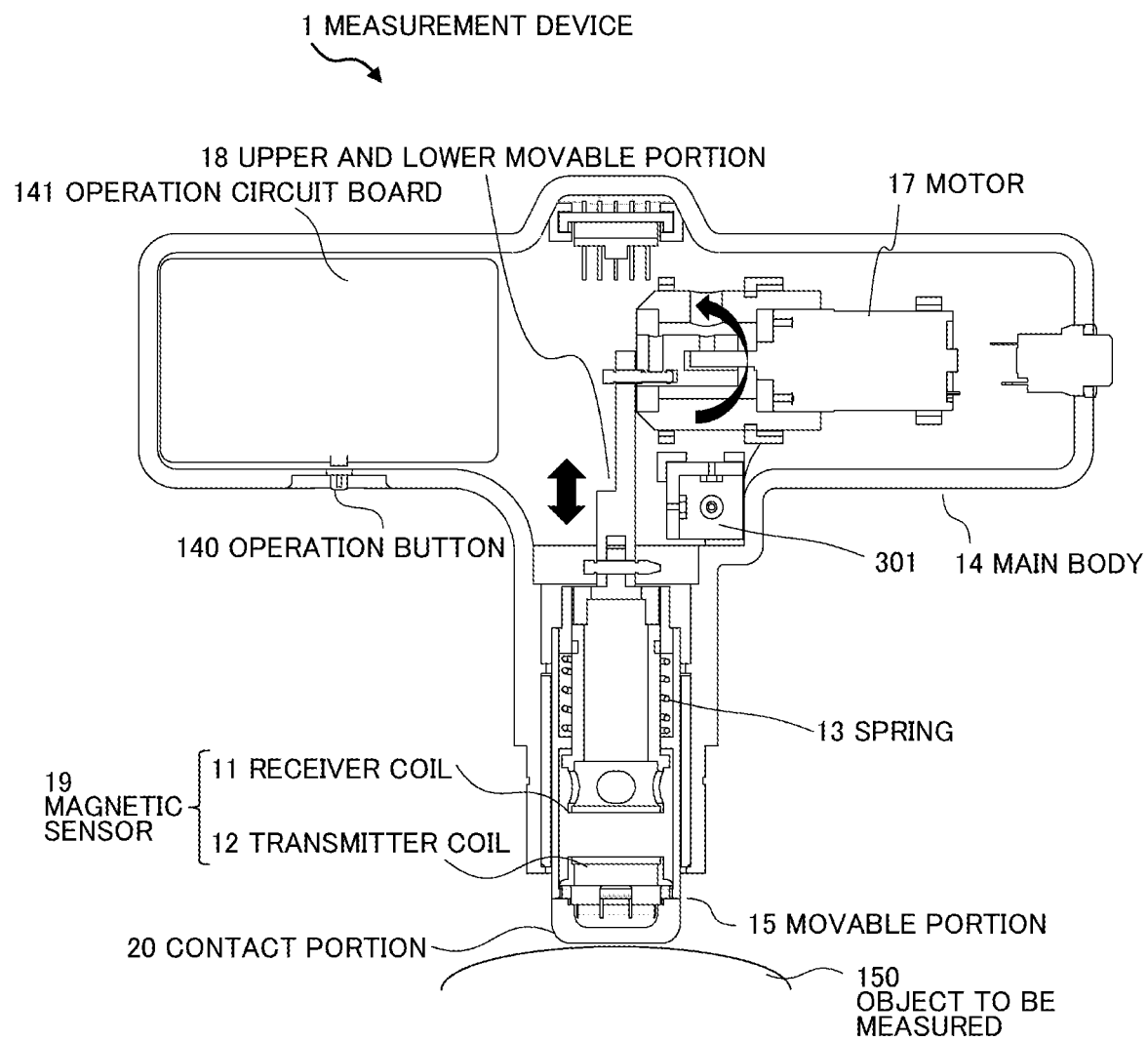
FIG. 3 is a description perspective view of an exemplary structure of a measurement device (T-shaped type).

FIG. 3 illustrates another exemplary configuration of the measurement device 1. In FIG. 2, the whole housing has an L shape, but may have a T shape or a pencil shape so that an operator can easily take it. FIG. 3 illustrates an example in the T shape. In FIG. 3, identical reference numbers are attached to the configurations in common with those in FIG. 2. A position measuring device 3 formed of a three-axis receiver coil 301 and a transmitter coil 302 will be described later.

Figure 4:
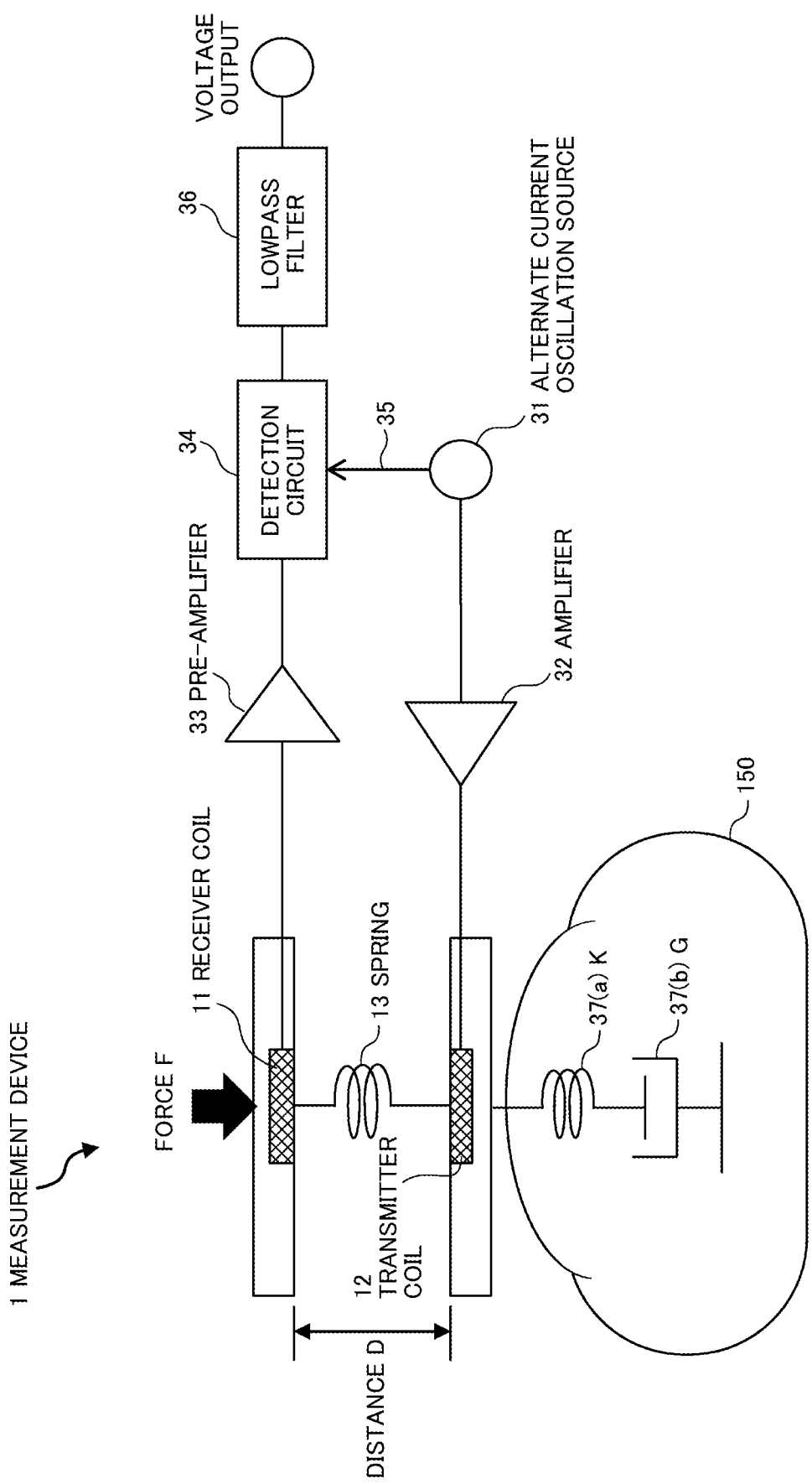
FIG. 4 is a schematic diagram of an operating principle of a measurement device.

A description will be given of operation of the magnetic sensor 19 and its peripheral components with reference to FIG. 4. First, an alternate current oscillation source 31 generates an AC voltage having a specific frequency (for example, 20 kHz). This AC voltage is converted into an alternating current having a specific frequency by an amplifier 32, and this converted alternating current flows through the transmitter coil 12. A magnetic field generated by the alternating current flowing through the transmitter coil 12 generates an induced electromotive force on the receiver coil 11.

An alternating current (having a frequency identical to the frequency of the AC voltage generated by the alternate current oscillation source 31) generated on the receiver coil 11 by the induced electromotive force is amplified by a pre-amplifier 33, and a signal after the amplification is input to a detection circuit 34. The detection circuit 34 detects the signal after the amplification at the specific frequency generated by the alternate current oscillation source 31 or its double frequency. Therefore, the output by the alternate current oscillation source 31 is introduced into a reference signal input terminal in the detection circuit 34 as a reference signal 35. An operation system using a full-wave rectifier circuit without the detection circuit 34 may be used. Information (output signal) on the voltage from the detection circuit 34 (or the rectifier circuit) is introduced into a driving circuit 21 (see FIG. 1) in the hardness calculating device 2 after passing through a lowpass filter 36.

The object 150 to be measured is modeled by a spring 37(a) having a spring constant K and a dashpot (damper) 37(b) having a dashpot coefficient G. The magnetic sensor 19 formed of the receiver coil 11 and the transmitter coil 12 is pressed against the object 150 to be measured. There is preferably a relationship of K'>K between the spring constant K' of the spring 13 and the spring constant K of the object 150 to be measured. Otherwise, when the main body 14 is compressed, the main body 14 possibly contacts the object 150 to be measured at the contact portion 20.

The following describes the hardness calculating device 2, returning to FIG. 1. The hardness calculating device 2 is a computer device. The hardness calculating device 2 includes the driving circuit 21, a microprocessor 23, a storage unit 24, an audio generation unit 25, a display unit 26, a power supply unit 27, an input unit 28, and a position estimation driving circuit 29.

The microprocessor 23 is achieved by, for example, a CPU (Central Processing Unit). The microprocessor 23 includes a voltage waveform generating unit 231, an abnormal waveform detecting unit 232, a voltage and pressure conversion unit 233, a hardness estimating portion 234, a determining unit 235, and a position estimating portion 236. The above-described processing units in the microprocessor 23 can be achieved by various programs. For example, in a memory (not illustrated) in the hardness calculating device 2, various programs stored in the storage unit 24 are deployed. The microprocessor 23 executes the program loaded into the memory to perform predetermined process and calculation. The following describes process contents by the respective processing units in the microprocessor 23.

The voltage waveform generating unit 231 generates waveform information of the output voltage of the magnetic sensor obtained from the driving circuit 21. An example of the waveform of the output voltage of the magnetic sensor will be described in detail later in FIG. 5.

The abnormal waveform detecting unit 232 detects an abnormal waveform in an inappropriate compression, for example, when the compression is too weak or too strong or when a compression direction is inclined with respect to an object surface. In the estimation of the hardness, a compression strength by the operator needs to be in an appropriate range. The abnormal waveform detecting unit 232 is intended to remove the waveform when the compression strength is out of this appropriate range.

As a detection method of the abnormal waveform, an abnormality can be determined under the condition that a magnitude of the direct current component of the output signal is out of a certain range. Alternatively, the abnormal waveform can be determined from undetectability of an upper limit and a lower limit of the alternating current component of the output signal. The detection of the hardness will be performed on the basis of the alternating current component of the output signal in a range where such abnormal waveform is not detected.

The voltage and pressure conversion unit 233 converts the output voltage of the magnetic sensor into pressure information. The output voltage of the magnetic sensor varies corresponding to a distance between the receiver coil 11 and the transmitter coil 12 in FIG. 2. This distance between the two coils is equal to a length of the spring 13. The reaction force applied to the spring can be calculated from a distance that the spring 13 shrinks from its free length and the spring constant of the spring 13 with Hooke's law. From these relationships, the output voltage of the magnetic sensor is converted into the pressure information. The conversion of the output voltage of the magnetic sensor into the pressure information will be described in detail later in FIG. 6 and FIG. 7.

Specifically, a magnetic flux at a distance between the predetermined two coils is calculated as follows. A slight line element on the receiver coil 11 is defined as ds1. A slight line element on the transmitter coil 12 is defined as ds2. A position vector of ds2 viewed from ds1 is defined as r. At this time, a mutual inductance $M_{12}$ of the receiver coil 11 and the transmitter coil 12 is calculated in the following formula (Neumann's formula). μ is a magnetic permeability.

[Formula 1]

$$M_{12} = \frac{\mu}{4\pi} \oint_{C1} \oint_{C2} \frac{ds_1 \cdot ds_2}{r} \quad \text{Formula 1}$$

When a current I flows through the receiver coil 11 and the number of turns of the receiver coil 11 is assumed as N, a magnetic flux φ inside the transmitter coil 12 is calculated as in the following formula using $M_{12}$.

[Formula 2]

$$\phi = N M_{12} I \quad \text{Formula 2}$$

Similarly, the magnetic fluxes φ when the distance between the two coils is varied by a predetermined distance will be calculated. The magnetic flux φ has a linear relationship with the output voltage of the magnetic sensor. Accordingly, from their data, a conversion curve of the distance between the two coils and the output voltage of the magnetic sensor can be created. Next, subtracting the distance between the two coils from the free length of the spring 13 obtains a displacement amount of the spring 13. This displacement amount is multiplied by the spring constant of the spring 13 to obtain the reaction force. As described above, a conversion curve of the output voltage of the magnetic sensor and the reaction force can be created.

<Method of Estimating Hardness>

The hardness estimating portion 234 will be described by referring to FIG. 5 to FIG. 10.

Figure 5:
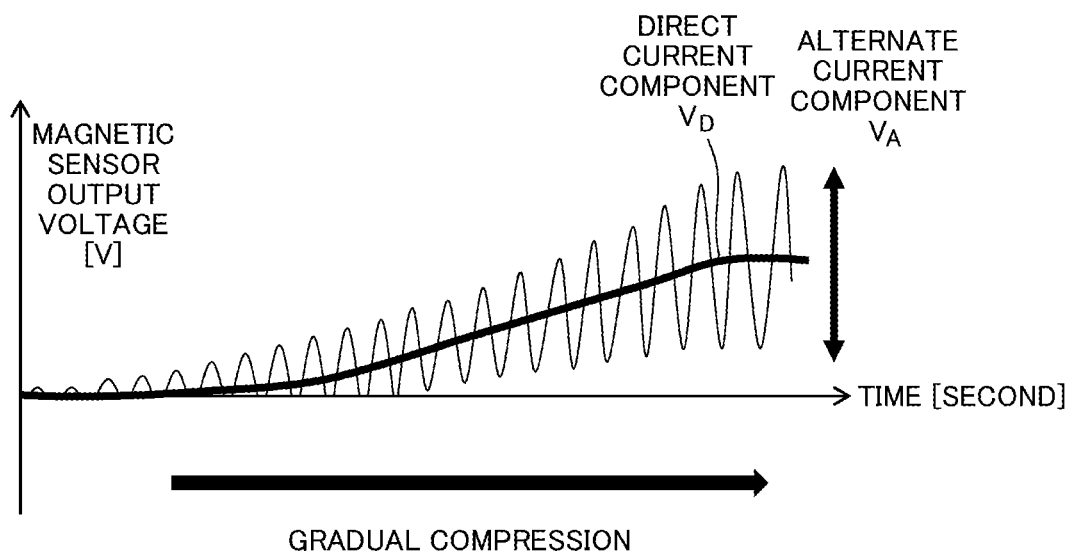
FIG. 5 is a schematic diagram of a voltage waveform of a magnetic sensor in the biological hardness meter.

FIG. 5 illustrates an output waveform of the magnetic sensor 19. The horizontal axis indicates a time (second) and the vertical axis indicates an output voltage (V). As the operator puts the biological hardness meter 1000 on the object 150 to be measured to proceed with compression little by little, a waveform of the output voltage of the magnetic sensor 19 as in FIG. 5 is obtained. For simplifying the condition, it is assumed that the hardness of the object 150 to be measured is constant regardless of the depth, that is, the hardness is uniform (similar in FIG. 6 to FIG. 9 as well). Here, a slow variation by the compression by hand excluding a frequency component of the motor 17 is referred to as a direct current component $V_D$, and an amplitude of a fast variation having the frequency component of the motor 17 is referred to as an alternating current component $V_A$. It is shown that, as the compression proceeds little by little, the direct current component $V_D$ increases, and in accordance with this, the alternating current component $V_A$ gradually increases. This is because, as the distance between the receiver coil 11 and the transmitter coil 12 decreases by the compression, the voltage of the magnetic sensor 19 exponentially increases. A known analog or digital frequency filter may be used for extraction of the direct current component and the alternating current component.

Figure 6:
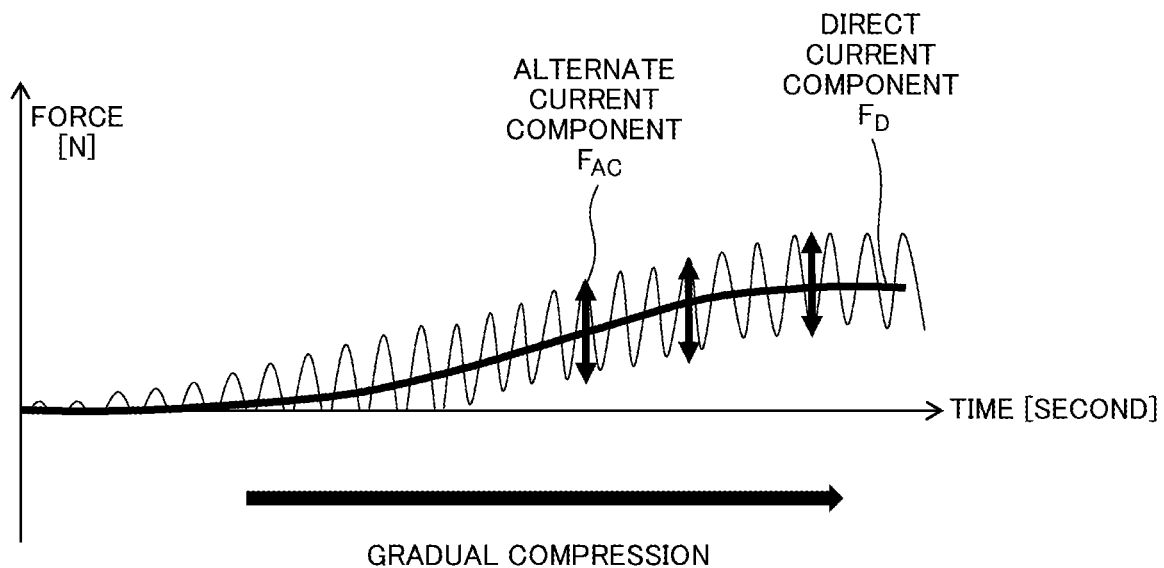
FIG. 6 is a schematic diagram when the voltage waveform of the magnetic sensor in the biological hardness meter is converted into a force.

FIG. 6 illustrates a waveform obtained such that the waveform of the output voltage of the magnetic sensor 19 is converted into a waveform of the pressure by the above-described voltage and pressure conversion unit 233. The horizontal axis indicates a time (second) similarly to FIG. 5, and the vertical axis indicates the converted pressure (N). In the pressure waveform, as the compression proceeds little by little, a direct current component $F_D$ increases, while an amplitude of an alternating current component $F_{AC}$ is always constant. The point that the alternating current component is constant is a difference with the output voltage of the magnetic sensor in FIG. 5. An estimated hardness is obtained on the basis of this alternating current component $F_{AC}$.

When actual hardness is obtained, a plurality of objects having known hardness are prepared. For each object, the biological hardness meter 1000 performs measurement to obtain the above-described amplitude of the alternating current component $F_{AC}$. This can make a correspondence table between the known hardness and the alternating current component $F_{AC}$. After an object having unknown hardness is measured and the alternating current component $F_{AC}$ is obtained, the alternating current component $F_{AC}$ can be converted into the hardness from this correspondence table. Data in the correspondence table is interpolated with a linear interpolation, a spline interpolation, or the like to obtain a conversion formula. Thus, even an alternating current component $F_{AC}$ that is not in the correspondence table can be converted into the hardness. A database of the above-described correspondence table is preliminarily made and stored as a database 1001 in, for example, the storage unit 24. The hardness estimating portion 234 refers the database 1001 to convert the pressure obtained from the voltage and pressure conversion unit 233 into the hardness.

Figure 7:
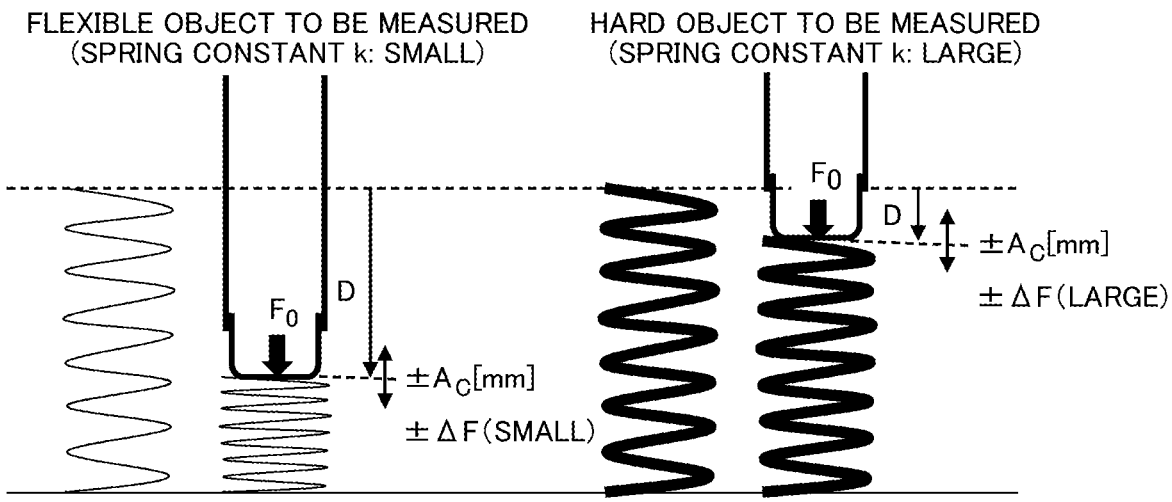
FIG. 7 is a principle explanatory view of a method of estimating hardness.

FIG. 7 is a principle explanatory view of a method of estimating the hardness. Here, the reason that the alternating current component $F_{AC}$ is considered as the estimated hardness in the pressure waveform in FIG. 6 will be described by referring to FIG. 7. When the operator compresses the object to be measured at a constant force $F_0$, a small periodic variation having an amplitude $A_C$ is further provided by the motor 17. When it is assumed that D is a push-in amount and ΔF is a variation amount (variation width) of the force in accordance with the periodic variation of the amplitude $A_C$, a relationship of $D:A_C=F_0:\Delta F$ is satisfied with the Hooke's law in this case.

This means that ΔF differs depending on the hardness of the object to be measured. That is, since the amplitude $A_C$ is constant, when the object 150 to be measured is flexible (the spring constant K of the object to be measured is small), the push-in amount D is large. Thus, a change in force ΔF by the amplitude $A_C$ of the motor 17 with respect to $F_0$ is small. Meanwhile, when the object to be measured is hard (the spring constant K of the object to be measured is large), the push-in amount D is small. Thus, the change in force ΔF by the amplitude $A_C$ of the motor 17 with respect to $F_0$ is large.

The following describes the above-described contents in a formula. When the spring constant of the object 150 to be measured is defined as K, a push-in amount D [mm] when the operator pushes the biological hardness meter 1000 at a certain force F is as follows with the Hooke's law.

$$F=KD$$

At this time, the motor 17 varies the contact portion 20 up and down at a predetermined amplitude $A_C$. At this time, when the operator pushes the biological hardness meter 1000 by hand at a predetermined force $F=F_D=KD_D$, the force when the motor 17 reaches highest position ($D_D-A_C$) is as follows.

$$F_U=K(D_D-A_C)=F-KA_C$$

Then, when the operator pushes the biological hardness meter 1000 by hand at the predetermined force $F=F_D=KD_D$, the force when the motor 17 reaches lowest position ($D_D+A_C$) is as follows.

$$F_L=K(D_D+A_C)=F+KA_C$$

A difference in force $F_{AC}$ (=the alternating current component of the force) between the highest position and the lowest position of the motor 17 is as follows.

$$F_{AC}=F_L-F_U=2KA_C$$

Since $A_C$ is constant, $F_{AC}$ is proportionate to the spring constant K of the object. Accordingly, it is shown that $F_{AC}$ increases as the object hardens. This formula shows that the alternating current component $F_{AC}$ of the force is always constant regardless of the compression strength (the direct current component of the force) insofar as the object has identical hardness.

A description will be given of a case where the hardness is estimated using the output voltage of the magnetic sensor directly as a force sensor, by referring to FIG. 8. In this case, the voltage and pressure conversion unit 233 is omitted, and the output voltage of the magnetic sensor 19 will be directly treated as the pressure. In this case, as a waveform illustrated in FIG. 8, in the magnetic sensor, as a direct current component $V_D$ increases (that is, as the compression strength strengthens), the alternating current component $V_A$ increases. This is, as described in the preceding paragraph, different from the point that the alternating current component of the force is always constant regardless of the direct current component of the force (the compression strength) when the voltage and pressure conversion unit 233 is exploited.

A cause that the alternating current component is thus not constant includes that the relationship between the output voltage and the force is not a proportional relation in the magnetic sensor. The distance between the two coils, which is between the transmitter coil 12 and the receiver coil 11, inside the hardness meter is equal to the length of the spring 13 inside the hardness meter. Thus, the distance between the two coils and the force have the linear relationship from the Hooke's law. Meanwhile, a magnitude of the magnetic flux does not have the linear relationship with the distance between the two coils, which is between the transmitter coil 12 and the receiver coil 11. There is a nonlinear relationship where the magnetic flux rapidly increases as the two coils approaches. Therefore, the force and the magnetic flux also have the nonlinear relationship. The alternating current component will increase as the compression strength strengthens.

Therefore, when the voltage and pressure conversion unit 233 is thus not exploited and the output voltage of the magnetic sensor is directly treated as the pressure, the alternating current component $V_{AC}$ of the voltage when the direct current component $V_D$ of the voltage is fixed at a constant value $V_{DC}$ is defined as the estimated hardness. This can estimate the hardness without depending on the nonlinear characteristic between the magnitude of the magnetic flux and the distance between the two coils.

Specifically, the database 1001 in the storage unit 24 stores the correspondence table of the amplitude of $V_{AC}$ and the hardness when the direct current component $V_D$ is fixed at the constant value $V_{DC}$. In the measurement, the direct current component $V_D$ is monitored to obtain the amplitude of the alternating current component $V_{AC}$ when the direct current component $V_D$ becomes the predetermined value $V_{DC}$. Then, the hardness corresponding to this amplitude is obtained with reference to the correspondence table.

An exemplary way to decide the constant value $V_{DC}$ will be described by referring to FIG. 8. When the measurement device 1 is gradually pressed against the object 150 to be measured to proceed with the compression, the alternating current component cannot be completely obtained in a range (A) where the hardness meter lightly touches the object 150 to be measured (a state where the direct current component $V_D$ of the voltage is small). On the one hand, an accurate value of the alternating current component cannot be obtained in a range (C) where the hardness meter has pressed the object to be measured to be saturated, since the object becomes hard as a rigid body. That is, the constant value $V_{DC}$ may be set at a voltage in a range (B) between above-described both completely opposite states so that the alternating current component is appropriately obtained in the voltage waveform. It is necessary to decide the constant value $V_{DC}$ again after the spring is replaced since it depends on the spring constant of the spring 13 inside the measurement device 1.

Figure 8:
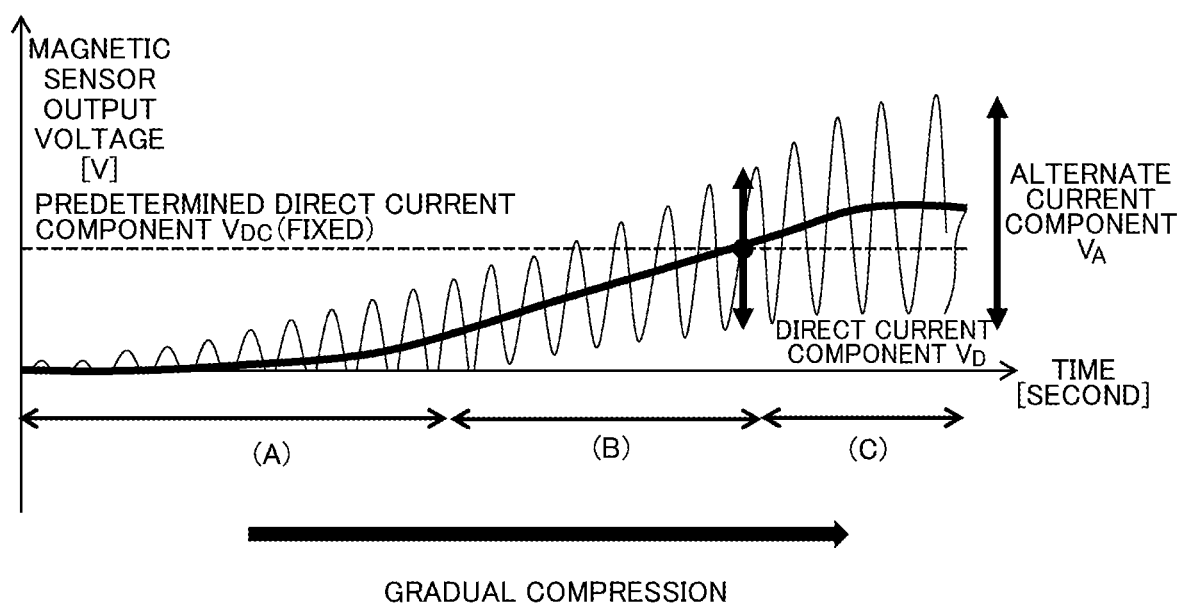
FIG. 8 is a schematic diagram that fixes a direct current component from an output waveform of the biological hardness meter to estimate the hardness.
Figure 9:
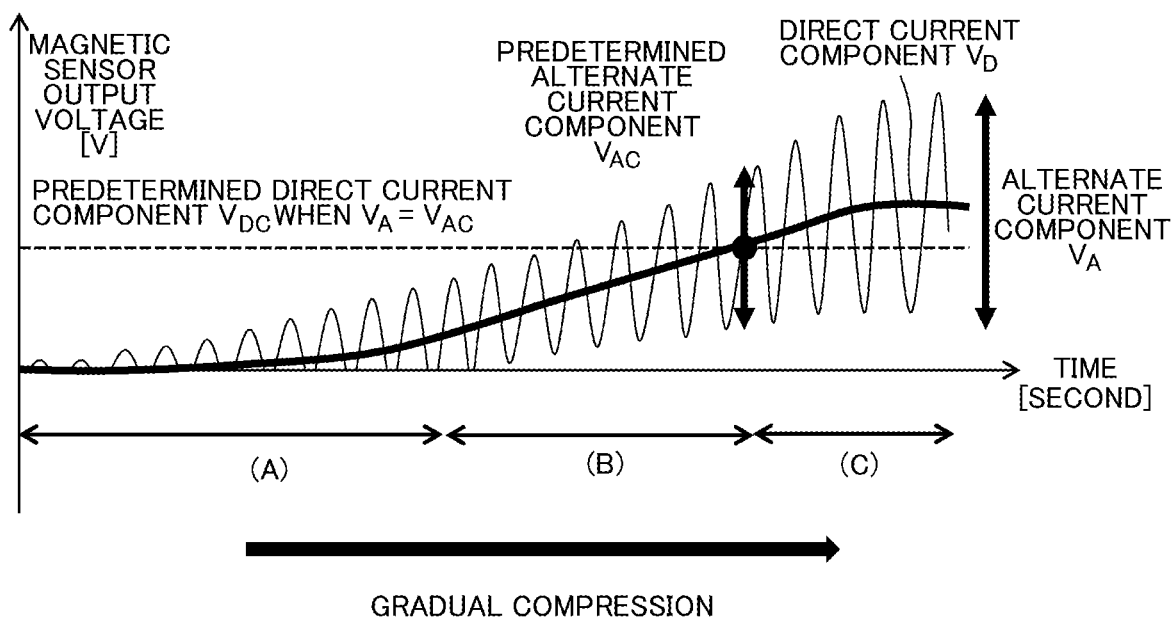
FIG. 9 is a schematic diagram that fixes an alternating current component from the output waveform of the biological hardness meter to estimate the hardness.

FIG. 9 illustrates another example. From a thought similar to that in FIG. 8, as illustrated in FIG. 9, the direct current component $V_{DC}$ of the voltage when the alternating current component $V_A$ of the voltage is fixed at the constant value $V_{AC}$ may be defined as the estimated hardness. This method also can estimate the hardness without depending on the nonlinear characteristic between the magnitude of the magnetic flux and the distance between the two coils. The direct current component $V_{AC}$ of the voltage also may be set at a direct current component of the voltage in the range (B) between both completely opposite states of the lightly contact state (A) and the strong pressed and saturated state (C) similarly to the above-described setting method of $V_{DC}$.

In FIG. 8 and FIG. 9, the description has been given of the methods of estimating the hardness on the basis of the alternating current component when the direct current component is fixed or the direct current component when the alternating current component is fixed, in the case where the voltage and pressure conversion unit 233 is not exploited. However, even in the case including the voltage and pressure conversion unit 233, the alternating current component of the force is not always constant depending on the property of the object to be measured. In this case, using the hardness estimation methods in FIG. 8 and FIG. 9 has a merit.

In FIG. 7, the description has been given by simplifying the object for which the hardness is estimated as having a characteristic identical to that of the spring. However, practically, it is assumed to measure a biological tissue such as skin, muscle, and adipose of the human body as the object. The spring accurately follows the Hooke's law, and the spring constant has a constant value regardless of the compression strength. However, it is known that the biological tissue, from its property, has a spring constant (hardness) that increases as being strongly compressed. Therefore, when the biological tissue is measured as the object, even after the output voltage of the magnetic sensor is converted into the force, the alternating current component $F_D$ is not constant as in FIG. 6 and may increase as the compression strengthens. From such reason, also when the voltage and pressure conversion unit 233 is exploited, the hardness may be estimated on the basis of the alternating current component when the direct current component is fixed (see FIG. 8) or the direct current component when the alternating current component is fixed (see FIG. 9). Further, several kinds of fixed values of the alternating current component and the direct current component may be set when the spring constant (hardness) differs depending on the compression strength.

Figure 10:
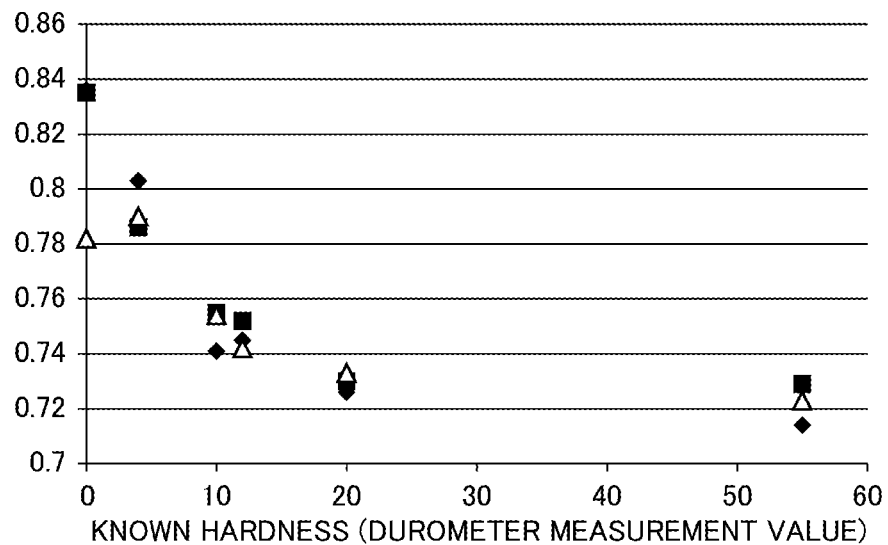
FIG. 10 is a graph illustrating a result of the estimation of the hardness.

FIG. 10 illustrates a result when the hardness is estimated in the method in FIG. 9 using the magnetic sensor 19 without the voltage and pressure conversion unit 233. Three kinds of markers in the graph represent three measurers. The horizontal axis is known hardness (no dimension) measured with the durometer, and the vertical axis is estimated hardness (V) obtained in the method in FIG. 9 with an electric hardness meter. From this graph, fitting is performed on data points of the estimated hardness and the known hardness with a polynomial to obtain a curve representing a relationship between the two. When the estimated hardness is obtained with the measurement with the electric hardness meter, the estimated hardness can be converted into the known hardness by plugging it in the curve.

Returning to FIG. 1, the storage unit 24, which is means for storing various kinds of information, is achieved by, for example, a RAM (Random Access Memory), a ROM (Read Only Memory), and an HDD (Hard Disk Drive). The storage unit 24 preliminarily stores a voltage and pressure conversion coefficient $C_{mp}$ calculated in an experiment. The audio generation unit 25, which is means for generating audio, is achieved by, for example, a speaker. The audio generation unit 25, for example, generates beep sound at the start and at the end of the measurement by the measurement device 1. The display unit 26, which is means for performing various displays, is achieved by, for example, an LCD (Liquid Crystal Display) or a CRT (Cathode Ray Tube) Display. The display unit 26 displays various waveforms, the hardness of the object (for example, at least one of elasticity information or viscosity information), and an indicator obtained by visualizing the hardness of the object.

The display unit 26 displays the estimated hardness obtained by the hardness estimating portion 234. As described later, this estimated hardness may be displayed in a color map at a measurement position on a biological surface. Here, the measurement position on the biological surface is, as described below, estimated by the position estimating portion 236 from magnetic field data on which position information obtained from the position measuring device is reflected. When the estimated hardness differs depending on the compression strength, the hardness may vary depending on a depth from the biological surface.

The display unit 26 also includes a compression instructing unit 261 that instructs the operator a compression method on the basis of the result of the abnormal waveform detecting unit 232. The compression instructing unit 261 instructs an appropriate compression strength when the abnormal waveform detecting unit 232 detects that the compression strength is inappropriate. The compression instructing unit 261 also instructs the appropriate compression strength when the hardness estimating portion 234 specifies the direct current component or the alternating current component as in FIG. 8 and FIG. 9.

The power supply unit 27 is power supply means in the hardness calculating device 2. The input unit 28, which is means operated by a user for inputting various kinds of information, is achieved by, for example, a keyboard and a computer mouse.

Returning to FIG. 2 and FIG. 3, the main body 14 includes the receiver coil 11, a coil substrate 110 mounting the receiver coil 11, the battery 16, an operation button 140 operated, for example, at the start to of hardness calculation, the motor 17, and an operation circuit board 141 connected to the receiver coil 11 and the transmitter coil 12. The movable portion 15 includes the transmitter coil 12 and a coil substrate 120 mounting the transmitter coil 12. One or a plurality of springs 13 are arranged between the coil substrate 110 and the coil substrate 120.

In the measurement device 1, when the motor 17 generates a rotational motion, a shaft mounted at a position shifted from an axis of the motor 17 rotates, and in accordance with this, the upper and lower movable portion 18 performs an up and down motion (crank mechanism). When the operation button 140 is pressed, the motor 17 starts rotating. When the press of the operation button 140 is stopped, the motor 17 stops rotating. This up and down motion periodically presses the movable portion 15 against the object to be measured. When the movable portion 15 is pressed against the object so that the object is depressed, the spring 13 shrinks to move the transmitter coil 12 close to the receiver coil 11, thus increasing the magnitude of the magnetic field detected by the receiver coil 11. This causes the receiver coil 11 to output the information on the voltage depending on the magnitude of the reaction force generated on the contact portion 20.

As described above, since the motor 17 stops rotating when the press of the operation button 140 is stopped, a stop position of the contact portion 20 will differ depending on a timing when the operator releases the operation button 140. Therefore, the photo sensor measures a rotation position of the motor 17 to take control so that the contact portion 20 always stops at a fixed position. Accordingly, the measurement device 1 has a hardware configuration identical to that of the durometer, and the direct current component of the waveform becomes identical to the output value of the durometer. The biological hardness meter 1000 will encompass the function of the durometer.

<Execution Order of Hardness Estimation Application>

Figure 11:
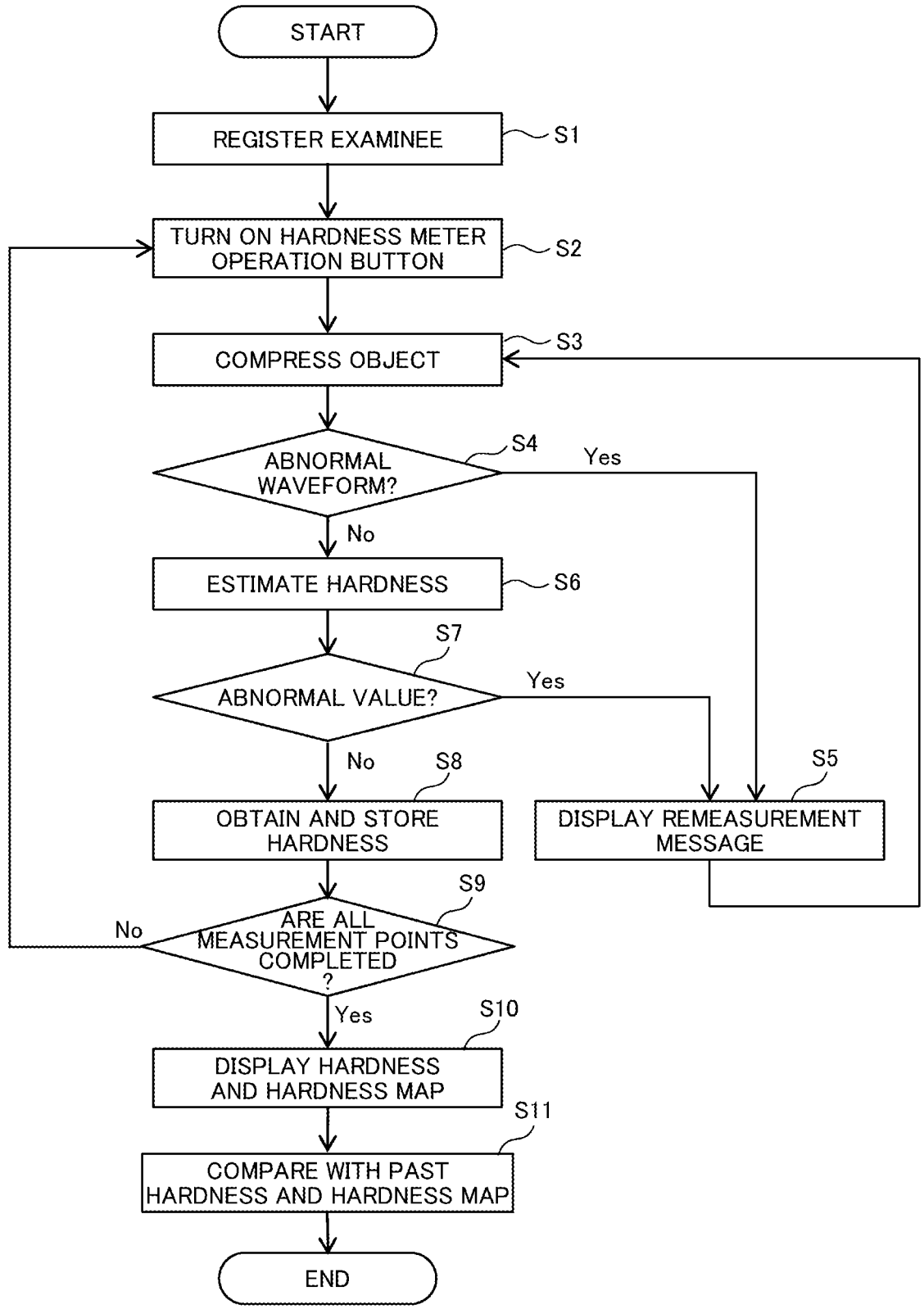
FIG. 11 is an exemplary flowchart illustrating a flow of a whole process by the biological hardness meter.

A description will be given of a process of the biological hardness meter 1000 with reference to a flowchart in FIG. 11 (see other drawings as necessary). The following describes by exemplifying a human body as the object to be measured. First, the operator registers an examinee whose hardness of body is measured (Step S1). Registered contents include an examinee ID, an examinee name, a gender, an age, disease information, therapy information, measurement result of other testing equipment, and the like.

FIG. 12 illustrates an exemplary registration screen.

Next, the hardness measurement of the human body is performed with the hardness meter. Specifically, when the operator turns on the operation button 140 of the measurement device 1, the motor 17 starts operating, and data of the magnetic sensor starts being recorded (Step S2). Here, the whole measurement device 1 is mounted on the motor 17. In a case of this configuration, driving the motor 17 can continuously press the movable portion 15 against the object at a predetermined frequency f Hz. For example, it may be set as f=about 2 to 8 Hz. Every time that the movable portion 15 of the measurement device 1 is pressed against the object 150 to be measured, the microprocessor 23 in the hardness calculating device 2 obtains information from this measurement device 1.

The operator gradually compresses the measurement device 1 to perpendicularly touch the surface of the human body in a state where the operation button 140 is in the on state (Step S3). Here, when the measured waveform of the magnetic sensor is abnormal, for example, when the compression strength is too strong or too weak, or when the measurement device 1 is inclined with respect to the surface of the human body, not perpendicular, the microprocessor 23 detects it (Step S4). This determination can be performed from, for example, the voltage of the direct current component of the magnetic sensor output voltage illustrated in FIG. 8 or the frequency of the alternating current component. This process is executed by the determining unit 235 of the microprocessor 23. In the case of Yes, the process proceeds to Step S5. In the case of No, the process proceeds to Step S6. When it is determined as the abnormal waveform, the microprocessor 23 displays a message of remeasurement on the display unit 26 to prompt the operator to appropriately modify the compression method (Step S5).

When it is determined as not the abnormal waveform in Step S4, the hardness is estimated (Step S6). The microprocessor 23 determines whether these values are abnormal values or not on the basis of the estimated value calculated in Step S3 (Step S7). This process is executed by the determining unit 235 of the microprocessor 23. In the case of Yes, the process proceeds to Step S5. In the case of No, the process proceeds to Step S8. The determination whether it is the abnormal value or not can be achieved by, for example, comparing an average value and a dispersion with preliminarily set thresholds.

In the case of No in Step S7, the estimated hardness is stored as a measurement value (Step S8). The process from Step S2 to Step S8 is repeated at a plurality of measurement points as necessary (Step S9). After the measurement at all the measurement points is completed, the microprocessor 23 displays a diagram obtained by mapping information regarding the hardness and the hardness on a human body schematic diagram, on the display unit 26 (Step S10).

FIG. 13 illustrates an example of this screen. In an example in FIG. 13(*a*), the hardness map shows the hardness at nine measurement points of the human body. The magnitude of the hardness can be expressed by light and shade or difference in color. As in FIG. 13(*b*), the hardness in different depths is expressed by a slide bar 1300. Further, comparison with past hardness or hardness map is ensured to evaluate therapy effect of, for example, acupuncture and moxibustion or massage (Step S11).

Thus, the display of a numerical value of the hardness at one certain position or the comparison with a past numerical value is ensured. Display of a hardness map including the hardness at a plurality of measurement positions or comparison with a past hardness map is also ensured. The measuring method in this embodiment can measure the hardness in different depths.

In order to measure the hardness in different depths, for example, in the data in FIG. 6, an alternating current component FAC1 at a timing when the direct current component is large and an alternating current component FAC2 at a timing when the direct current component is small are obtained to obtain each corresponding hardness. The alternating current component FAC1 at the timing when the direct current component is large reflects the hardness at a deep part. The alternating current component FAC2 at the timing when the direct current component is small reflects the hardness at a shallow part. As described above, since the graph in FIG. 6 postulates the uniform firmness, the magnitude of the alternating current component is identical at any position. However, when the hardness differs depending on the depth, the magnitude of the alternating current component will differ depending on the magnitude of the direct current component.

In a system to directly use the output of the magnetic sensor as in FIG. 8 and FIG. 9, taking a plurality of fixed points can measure a plurality of depths.

FIGS. 14A and 14B are tables illustrating exemplary correspondence tables included in the database 1001 in the embodiment.

FIG. 14A includes exemplary correspondence tables that convert the waveform of the output voltage of the magnetic sensor 19 into the waveform of the pressure and convert the pressure waveform into the hardness as in FIG. 6. FIG. 14A(a) is a correspondence table between the direct current component amplitude and the depth. FIG. 14A(b) is a correspondence table between the alternating current component amplitude and the hardness. These tables may be, for example, experimentally obtained in advance. When the hardness of a given depth is desired to be measured, the direct current component amplitude corresponding to the depth is obtained in FIG. 14A(a), and the alternating current component amplitude at a timing of this direct current component amplitude is obtained. Then, the hardness corresponding to the alternating current component amplitude is obtained in FIG. 14A(b).

FIG. 14B includes exemplary correspondence tables when the hardness is estimated using the output voltage of the magnetic sensor directly as the force sensor as in FIG. 8. In the example in FIG. 8, the alternating current component $V_{AC}$ of the voltage when the direct current component $V_D$ of the voltage is fixed at the constant value $V_{DC}$ is defined as the estimated hardness. In this case, since the correspondence between the alternating current component amplitude and the hardness differs depending on the magnitude of the direct current component, that is, the depth, a plurality of correspondence tables are necessary depending on the depth. FIG. 14B(a) is a correspondence table between the alternating current component amplitude at the shallow part (the magnitude of the direct current component is 100 mV) and the hardness. FIG. 14B(b) is a correspondence table between the alternating current component amplitude at the deep part (the magnitude of the direct current component is 200 mV) and the hardness.

As in FIG. 9, when the hardness is estimated on the basis of the direct current component when the alternating current component is fixed, a correspondence table between the direct current component and the hardness will be prepared corresponding to a plurality of alternating current components. Here, the hardness in the correspondence table may be the estimated hardness or a value obtained by converting the estimated hardness into the known hardness as described in FIG. 10.

Figure 15:
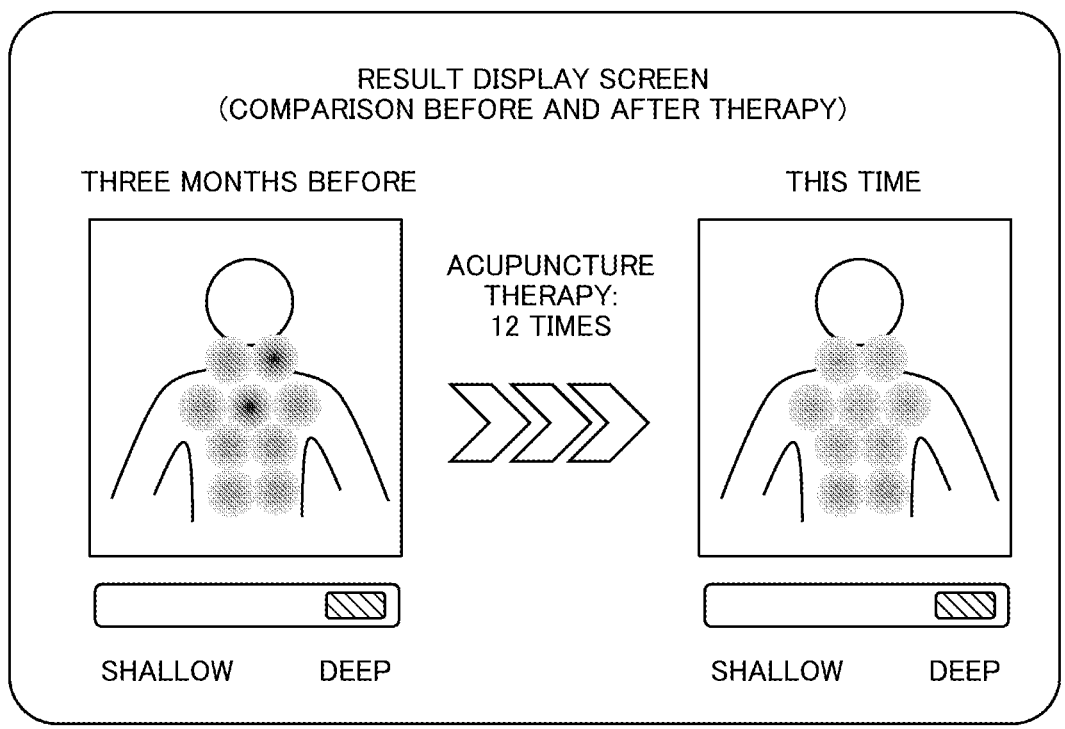
FIG. 15 is a diagram illustrating the hardness maps before and after a therapy in the result display screen.

FIG. 15 illustrates an exemplary screen displaying comparison of past data with latest data. Hardness information and the hardness map may be displayed side-by-side, or difference in both may be displayed. As described above, all steps end.

<Estimation of Measurement Position>

The following describes a method of obtaining measurement position information required for map display of the estimated hardness on the display unit 26. The position measuring device 3 illustrated in FIG. 1 is configured from, for example, five transmitter coils 302 and the three-axis receiver coil 301.

FIG. 16 is an arrangement schematic diagram of the five transmitter coils 302 and the three-axis receiver coil 301. Here, the number of transmitter coils 302 is five, but may be another number insofar as the number required for obtaining the position information as a target. The three-axis receiver coil 301 is internally mounted on the biological hardness meter 1000. The five transmitter coils 302 are defined as ones whose positional relationship with the object to be measured is already-known. The transmitter coil 302 is arranged on, for example, a sample stage on which the object 150 to be measured is arranged. When the object 150 to be measured is the human body, the transmitter coil 302 may be incorporated in a bed. This can estimate the measurement position of the biological hardness meter with respect to the transmitter coil.

The position measuring device 3 has a measurement principle similar to that of the measurement device 1. The position estimation driving circuit 29 applies the current to the transmitter coil 302 to generate the magnetic field in its peripheral area. This magnetic field generates the voltage on the three-axis receiver coil 301 with an electromagnetic induction principle. Unlike the measurement device 1, since there are both a plurality of receiver coils and transmitter coils, interference of the magnetic field is a problem. This problem is solved with a method of employing a time-sharing system that switches applying and detecting the current in respective combinations (15 patterns) of the transmitter coil and the receiver coil in a short time. As another method, when the current is simultaneously applied to a plurality of transmitter coils, varying the frequency of the transmitter coil ensures the detection without mutual interference of the magnetic fields of the plurality of transmitter coils.

The position estimating portion 236 calculates the position information required for the map display of the estimated hardness on the biological surface on the display unit 26. Three-dimensional positions (horizontal directions X and Y, a perpendicular direction Z) and attitude angles (an elevation angle θ, an azimuth angle φ) of the three-axis receiver coil are estimated from the obtained magnetic field data with a simulation of the magnetic field. When the estimated hardness is displayed on the display unit 26, for example, when the estimated hardness is mapped on a schematic diagram of a back of the human body, the estimated hardness may be displayed in a color map using only the position information in the horizontal directions X and Y. In addition, when the estimated hardness is three-dimensionally displayed in a map on a face surface, the estimated hardness may be displayed in a map using the position information of X, Y, and Z.

In this embodiment, the magnetic field measurement is used for estimating the position, but another method may be used. For example, the measurement position may be estimated by shooting with camera. The measurement position may be estimated with double integral in an acceleration sensor.

According to this embodiment described above, in the hardness meter including the main body including the movable portion continuously pressed against the object to be measured, the pressure sensor that outputs the reaction force information corresponding to the reaction force at the part of the object to be measured that is in contact with the movable portion, the motor, and the crank mechanism driven by the motor to cause the main body and the movable portion to perform the piston motion, the hardness estimating portion that estimates the hardness on the basis of the alternating current component of the pressure sensor value generated from the piston motion by the movable portion is provided.

In this embodiment, the magnetic sensor is used as the pressure sensor, but another type sensor may be used. For example, instead of the magnetic sensor 19 in FIG. 2, a piezoresistive pressure sensor using a semiconductor process can be arranged. The piezoresistive pressure sensor, which has a semiconductor strain gauge on a surface of a diaphragm, converts change in electrical resistance with a piezoresistive effect generated such that the diaphragm is deformed by the force (pressure) from outside into an electrical signal. In view of this, the information on the force illustrated in FIG. 6 can be obtained directly from output of this sensor.

The present invention is not limited to the above-described embodiment and includes various modifications. The above-described embodiments have been described in detail in order to easily describe the present invention, and therefore, it is not necessarily limited to include all the described configurations. It is possible to replace a part of the configuration of one embodiment with a configuration of another embodiment, and it is possible to add a configuration of one embodiment to a configuration of another embodiment. Some of the configurations of each embodiment can be added to, deleted from, or replaced by other configurations.

The above-described various processes of the microprocessor 23 may be ensured by hardware such that some of or all of which are designed with, for example, an integrated circuit. The above-described respective configurations, functions, and the like may be ensured by software such that a processor interprets and executes a program that ensures respective functions. Information such as a program, a table, and a file that ensure respective functions can be stored in a recording device such as a memory, a hard disk, and an SSD (Solid State Drive) and a recording medium such as an IC card, an SD card, and a DVD.

In the above-described embodiment, control lines and information lines considered necessary for the explanation are described. All of the control lines and the information lines of the product are not necessarily described. All configurations may be mutually coupled.

INDUSTRIAL APPLICABILITY

The present invention can be used for a hardness meter that estimates hardness of an object.

REFERENCE SIGNS LIST

1 . . . measurement device,
2 . . . hardness calculating device,
11 . . . receiver coil,
12 . . . transmitter coil,
13 . . . spring,
14 . . . main body,
15 . . . movable portion,
16 . . . battery,
17 . . . motor,
18 . . . upper and lower movable portion,
19 . . . magnetic sensor,
20 . . . contact portion,
21 . . . driving circuit,
23 . . . microprocessor,
24 . . . storage unit,
25 . . . audio generation unit,
26 . . . display unit,
27 . . . power supply unit,
28 . . . input unit,
3 . . . position measuring device,
31 . . . alternate current oscillation source,
32 . . . amplifier,
33 . . . pre-amplifier,
34 . . . detection circuit,
35 . . . reference signal,
36 . . . lowpass filter,
37(a) . . . spring,
37(b) . . . dashpot,
110, 120 . . . coil substrate,
140 . . . operation button,
141 . . . operation circuit board,
130 . . . operation circuit board,
140 . . . operation button,
231 . . . voltage waveform generating unit,
232 . . . abnormal waveform detecting unit,
233 . . . voltage and pressure conversion unit,
234 . . . hardness estimating portion,
235 . . . determining unit,
236 . . . position estimating portion,
261 . . . compression instructing unit,
301 . . . three-axis receiver coil,
302 . . . transmitter coil,
1000 . . . biological hardness meter

The invention claimed is:

1. A hardness meter comprising:
a movable portion which is continuously pressed against an object to be measured;
a sensor which outputs an output signal reflecting a reaction force at a part of the object to be measured that is in contact with the movable portion;
a motive force mechanism that causes the movable portion to perform a piston motion; and
a hardness estimating portion which estimates the hardness of the object to be measured on the basis of an alternating current component of the output signal, generated by the piston motion of the movable portion,
wherein the hardness estimating portion estimates the hardness of the object to be measured on the basis of an amplitude of the alternating current component of the output signal, and
wherein the hardness estimating portion estimates the hardness of the object to be measured on the basis of the amplitude of the alternating current component when a magnitude of a direct current component of the output signal is fixed at a predetermined value.

2. The hardness meter according to claim 1,
wherein the hardness estimating portion estimates the hardness of the object to be measured on the basis of a magnitude of a direct current component when the amplitude of the alternating current component of the output signal is fixed at a predetermined value.

3. The hardness meter according to claim 1 comprising an abnormal waveform detecting unit which detects an abnormal waveform under a condition that a magnitude of a direct current component of the output signal is out of a certain range,
wherein the hardness estimating portion estimates the hardness of the object to be measured on the basis of the alternating current component of the output signal in a range where the abnormal waveform is undetected at the abnormal waveform detecting unit.

4. The hardness meter according to claim 1, comprising an abnormal waveform detecting unit which detects an abnormal waveform under a condition that an upper limit and a lower limit of the alternating current component of the output signal are undetectable,
wherein the hardness estimating portion estimates the hardness of the object to be measured on the basis of the alternating current component of the output signal in a range where the abnormal waveform is undetected at the abnormal waveform detecting unit.

5. The hardness meter according to claim 1 comprising a voltage and pressure conversion unit which converts an output voltage of the sensor into pressure information.

6. The hardness meter according to claim 1 comprising:
a position estimating portion which estimates a measurement position of the hardness meter; and
a hardness map display unit which displays the hardness estimated using the measurement position in a map.

7. The hardness meter according to claim 6,
wherein the hardness map display unit presents a difference between two hardness maps.

8. A hardness measuring method comprises:
a first step of vibrating a movable portion;
a second step of obtaining a sense signal on the basis of a reaction force from an object to be measured when the movable portion is caused to contact the object to be measured;
a third step of obtaining an alternating current component of the sense signal; and
a fourth step of estimating hardness of the object to be measured on the basis of an amplitude of the alternating current component,
wherein a vibration member which vibrates the movable portion is used, and the vibration member is coupled to the movable portion via a spring in the first step,
wherein the sense signal is obtained on the basis of a magnetic sensor signal detected such that a first coil arranged on the movable portion and a second coil arranged on the vibration member are used and a signal transmitted from one coil is received at the other coil in the second step, wherein the method uses a computer device including a microprocessor, a storage unit, an input unit, and an output unit, wherein the microprocessor converts a waveform of the magnetic sensor signal obtained from the input unit into a waveform of a pressure with a voltage and pressure conversion to obtain the sense signal, wherein the method which prepares a correspondence table between the amplitude of the alternating current component of the sense signal and the hardness as a database in the storage unit, and wherein the microprocessor estimates the hardness on the basis of the correspondence table.

9. A hardness measuring method comprises:

a first step of vibrating a movable portion;

a second step of obtaining a sense signal on the basis of a reaction force from an object to be measured when the movable portion is caused to contact the object to be measured;

a third step of obtaining an alternating current component of the sense signal; and a fourth step of estimating hardness of the object to be measured on the basis of an amplitude of the alternating current component, wherein a vibration member which vibrates the movable portion is used, and the vibration member is coupled to the movable portion via a spring in the first step, wherein the sense signal is obtained on the basis of a magnetic sensor signal detected such that a first coil arranged on the movable portion and a second coil arranged on the vibration member are used and a signal transmitted from one coil is received at the other coil in the second step, wherein the method uses a computer device including a microprocessor, a storage unit, an input unit, and an output unit, and wherein the microprocessor uses a waveform of the magnetic sensor signal directly as the sense signal.

10. The hardness measuring method according to claim 9 which prepares a correspondence table between an amplitude of the sense signal and the hardness as a database in the storage unit, wherein the correspondence table shows a correspondence between an amplitude of the alternating current component of the sense signal and the hardness when a direct current component of the sense signal is fixed or shows a correspondence between an amplitude of the direct current component of the sense signal and the hardness when the alternating current component of the sense signal is fixed, and the microprocessor estimates the hardness on the basis of the correspondence table.

* * * * *